(12) United States Patent
Kajihara (10) Patent No.: US 11,226,291 B2
(45) Date of Patent: Jan. 18, 2022

(54) BIOLOGICAL SUBSTANCE ANALYSIS METHOD, BIOLOGICAL SUBSTANCE ANALYZER, AND BIOLOGICAL SUBSTANCE ANALYSIS SYSTEM

(71) Applicant: SONY CORPORATION, Tokyo (JP)

(72) Inventor: Junji Kajihara, Tokyo (JP)

(73) Assignee: SONY CORPORATION, Tokyo (JP)

( * ) Notice: Subject to any disclaimer, the term of this patent is extended or adjusted under 35 U.S.C. 154(b) by 126 days.

(21) Appl. No.: 16/486,642

(22) PCT Filed: Dec. 18, 2017

(86) PCT No.: PCT/JP2017/045236
§ 371 (c)(1),
(2) Date: Aug. 16, 2019

(87) PCT Pub. No.: WO2018/168137
PCT Pub. Date: Sep. 20, 2018

(65) Prior Publication Data
US 2020/0056995 A1    Feb. 20, 2020

(30) Foreign Application Priority Data
Mar. 16, 2017   (JP) .............................. JP2017-051096

(51) Int. Cl.
*G01N 21/64*   (2006.01)
*G01N 33/543*   (2006.01)
(Continued)

(52) U.S. Cl.
CPC ..... *G01N 21/6428* (2013.01); *G01N 21/6456* (2013.01); *G01N 33/54306* (2013.01);
(Continued)

(58) Field of Classification Search
CPC ......... G01N 21/6428; G01N 33/54306; G01N 2021/6439; G01N 33/54373;
(Continued)

(56) References Cited

U.S. PATENT DOCUMENTS 6,483,641 B1    11/2002   MacAulay
7,525,727 B2 *   4/2009   Sander .................... G02B 21/22
                                                    359/388
(Continued)

FOREIGN PATENT DOCUMENTS

AU    2009300369 A1   4/2010
CA    2738626 A1   4/2010
(Continued)

OTHER PUBLICATIONS

Translation of JP2018021894A, Kato et al., Feb. 8, 2018 (publication related to foreign priority of US20180025475A1) (Year: 2018).*
(Continued)

*Primary Examiner* — Samuel P Siefke
*Assistant Examiner* — Henry H Nguyen
(74) *Attorney, Agent, or Firm* — Chip Law Group (57) ABSTRACT

The present technology provides an irradiation method, a biological substance analysis method, and a biological substance analyzer to improve a throughput while securing signal reliability of detection data when a biological substance is caught on a substrate and the biological substance is detected by irradiating the substrate. For this, the present technology provides a biological substance analysis method and the like including: a step of segmenting a substrate on which a molecule that can be bound to a biological substance is immobilized and the biological substance is bound to the molecule, and irradiating the substrate in accordance with an irradiation pattern having a different segment with time; and (Continued)

a step of analyzing the biological substance on the basis of information obtained from the irradiation.

11 Claims, 6 Drawing Sheets

(51) Int. Cl.
*G02B 21/06* (2006.01)
*G02B 21/00* (2006.01)

(52) U.S. Cl.
CPC ............... *G01N 2021/6439* (2013.01); *G01N 2201/0635* (2013.01); *G02B 21/006* (2013.01); *G02B 21/06* (2013.01)

(58) Field of Classification Search
CPC ....... G01N 21/6456; G01N 2201/0635; G01N 37/00; C12M 1/00; G16B 40/10; G02B 21/006; G02B 21/06
See application file for complete search history.

(56) References Cited

U.S. PATENT DOCUMENTS

| | | | | |
|---|---|---|---|---|
| 2010/0066823 | A1* | 3/2010 | Westphal | G02B 21/16 348/79 |
| 2010/0099100 | A1 | 4/2010 | Zaccarin et al. | |
| 2012/0225448 | A1 | 9/2012 | Sugiyama et al. | |
| 2016/0320600 | A1* | 11/2016 | Dake | G02B 21/082 |
| 2018/0025475 | A1* | 1/2018 | Kato | G06T 5/002 348/241 |

FOREIGN PATENT DOCUMENTS

| | | |
|---|---|---|
| CN | 102227659 A | 10/2011 |
| CN | 102666851 A | 9/2012 |
| EP | 1207414 A1 | 5/2002 |
| EP | 1207415 A1 | 5/2002 |
| EP | 2362947 A2 | 9/2011 |
| EP | 2500424 A1 | 9/2012 |
| JP | 2001-521205 A | 11/2001 |
| JP | 2006-071417 A | 3/2006 |
| JP | 2006-171024 A | 6/2006 |
| JP | 2015-084059 A | 4/2015 |
| TW | 201106032 A | 2/2011 |
| WO | 99/22262 A1 | 5/1999 |
| WO | 2010/039199 A2 | 4/2010 |
| WO | 2011/058721 A1 | 5/2011 |

OTHER PUBLICATIONS

International Search Report and Written Opinion of PCT Application No. PCT/JP2017/045236, dated Feb. 27, 2018, 09 pages of ISRWO.

* cited by examiner

BIOLOGICAL SUBSTANCE ANALYSIS METHOD, BIOLOGICAL SUBSTANCE ANALYZER, AND BIOLOGICAL SUBSTANCE ANALYSIS SYSTEM

CROSS REFERENCE TO RELATED APPLICATIONS

This application is a U.S. National Phase of International Patent Application No. PCT/JP2017/045236 filed on Dec. 18, 2017, which claims priority benefit of Japanese Patent Application No. JP 2017-051096 filed in the Japan Patent Office on Mar. 16, 2017. Each of the above-referenced applications is hereby incorporated herein by reference in its entirety.

TECHNICAL FIELD

The present invention relates to a biological substance analysis method, a biological substance analyzer, a biological substance analysis program, and a biological substance analysis system, in which a substrate on which a molecule that can be bound to a biological substance is immobilized is used.

BACKGROUND ART

In recent years, a cell analysis/sorting apparatus, a chip and the like to analyze biopolymers such as DNA are developed.

As the cell analysis/sorting apparatus, there is a type in which a cell is caught on a device of the apparatus, a two-dimensional image is obtained by irradiation, and the cell is sorted.

As the biopolymer analysis chip, there is a type in which a biopolymer is caught on the chip, a two-dimensional image is obtained by irradiation, and the biopolymer is analyzed.

As a base material of the device used in the cell analysis/sorting apparatus, for example, it is possible to exemplify a cell-adhesive photo-controllable base material obtained by depositing a cell-adhesive photo-controllable material on a base material, in which the cell-adhesive photo-controllable material is obtained by binding a cell adhesive material to a cell non-adhesive material via a photo-dissociable group (Patent Document 1).

A cell bound to the device disclosed in Patent Document 1 is detected by two-dimensional scanning by using a two-dimensional CCD camera or a photomultiplier tube while condensing excitation light or by using a line sensor through a dispersive element.

As the biopolymer analysis chip, for example, it is possible to exemplify a chip including: a solid-state imaging device; an optical transmission unit that transmits an image from one surface to the other surface thereof and is arranged on a light receiving surface of the solid-state imaging device in a manner such that the one surface thereof faces the light receiving surface of the solid-state imaging device; and a plurality of kinds of spots including known biopolymers and scattered along the other surface of the optical transmission unit (Patent Document 2).

The biopolymers bound to the chip disclosed in Patent Document 2 are detected by: applying a fluorescent-labeled sample onto the other surface of the optical transmission unit; binding the sample to a specific spot preliminarily immobilized on an excitation light shielding film on the other surface of the optical transmission unit; making fluorescence intensity distribution appear on the other surface of the optical transmission unit by emitting the excitation light toward the other surface; transmitting, as an image, the fluorescence intensity distribution from the other surface to the one surface; and imaging the entire surface with the solid-state imaging device at a time.

CITATION LIST

Patent Document

Patent Document 1: International Publication No. WO2011/058721
Patent Document 2: Japanese Patent Application Laid-Open No. 2006-71417

SUMMARY OF THE INVENTION

Problems to be Solved by the Invention

However, in a case of scanning the device as disclosed in Patent Document 1, there is a problem that a time lag is generated in an observation time depending on a position inside a surface because image data is obtained by irradiating the entire surface of the device while shifting the position from one end to the other end of the device. Additionally, scanning takes a long time, and data cannot be obtained at a time at a high throughput.

Furthermore, in a case of imaging an entire surface at a time as disclosed in Patent Document 2, the problem like Patent Document 1 does not occur because the surface is irradiated, however; in a case where a distance between fluorescent-labeled samples is short, fluorescence overlaps and crosstalk in which signals from an optical transmission unit affect each other occurs. Since the crosstalk may deteriorate signal quality or may cause false detection, there is a limit in densely binding the fluorescent-labeled samples.

Figure 1:
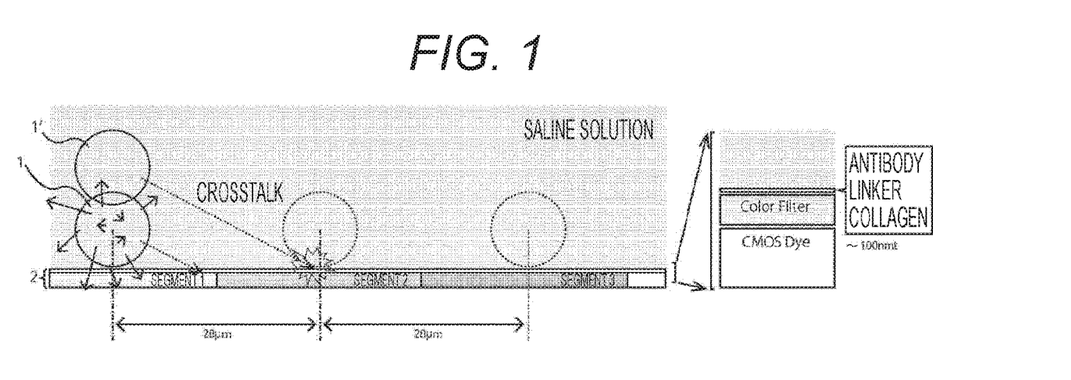
FIG. 1 is a conceptual diagram to describe crosstalk.

The crosstalk problem can be illustrated like FIG. 1, for example.

Assuming that the fluorescent-labeled sample described in Patent Document 2 is a cell, a fluorescent-labeled cell 1 is bound to a segment 1 via an antibody or the like on a substrate 2. The fluorescent-labeled cell 1 emits fluorescence in all directions as indicated by thick arrows.

When the fluorescent-labeled cell 1 is detected by a solid-state imaging device (CMOS dye) of the substrate, in a case where fluorescence from the fluorescent-labeled cell 1 reaches a segment 2 and a segment 3 (dotted lines in FIG. 1), the fluorescence is also detected by solid-state imaging devices in the segment 2 and the segment 3, and therefore, the fluorescent-labeled cell 1 is erroneously detected as being bound not only to the segment 1 but also to the segment 2 and the segment 3.

Furthermore, when a distance from the solid-state imaging device to the fluorescent-labeled cell is increased and becomes a height of a fluorescent-labeled cell 1' in FIG. 1, for example, the fluorescence of the fluorescent-labeled cell 1' reaches farther. Accordingly, the increase in the distance from the surface of the solid-state imaging device to the cell leads to deterioration of a Signal to Noise ratio (S/N).

Here, as a factor that increases the distance from the solid-state imaging device to the fluorescent-labeled cell, forming a color filter thick in order to secure spectral characteristics of the color filter on the solid-state imaging device, or the like can be considered.

Figure 2:
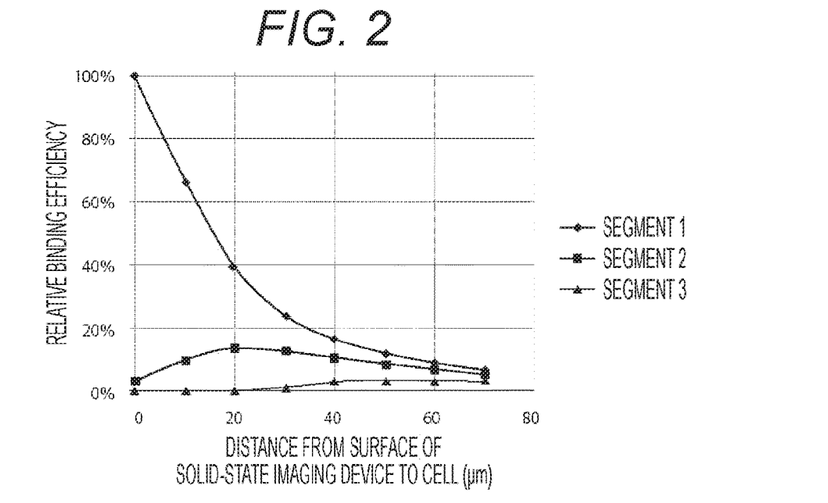
FIG. 2 is a graph illustrating changes in a fluorescence detection signal amount based on a distance from a surface of a solid-state imaging device to each cell.

FIG. 2 illustrates changes in a fluorescence detection signal amount based on the distance from the surface of the solid-state imaging device to each cell. Assuming that relative binding efficiency (a signal amount) is 100% when the fluorescent-labeled cell 1 contacts the color filter (4 μm) (distance 0 μm), the more the distance is increased (the higher the position of the fluorescent-labeled cell is), the weaker a detection signal in the segment 1 is. When the distance becomes 20 μm, the detection signal in the segment 1 is decreased to about 40%, and a detection signal in the segment 2 is increased by about 15%. When the distance becomes further increased, the detection signals in the segment 1 and the segment 2 tend to be decreased, and the detection signal in the segment 3 tends to be slightly increased.

Figure 3:
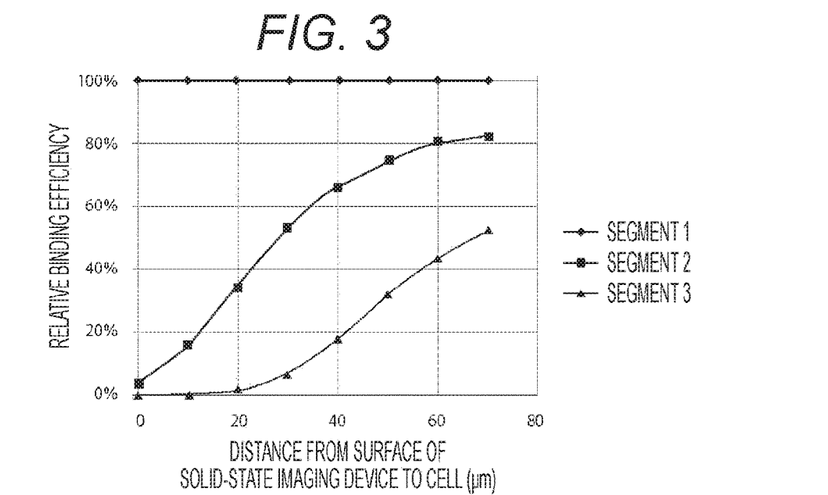
FIG. 3 is a graph illustrating changes in a crosstalk amount based on the distance from the surface of the solid-state imaging device to each cell.

FIG. 3 illustrates changes in a crosstalk amount based on the distance from the surface of the solid-state imaging device to each cell.

Assuming that the relative binding efficiency (signal amount) in the segment 1 is 100%, the more the distance from the surface of the solid-state imaging device to the fluorescent-labeled cell is increased, the more the signal amounts in the segment 2 and the segment 3 are increased. From this fact, it can be grasped that a possibility of false detection in the segment 2 and the segment 3 is increased when the distance is increased.

Such a crosstalk problem tends to occur particularly when the entire surface of the substrate is irradiated at a time.

Solutions to Problems

To solve the above-described problem, the present technology provides a biological substance analysis method including:

a step of segmenting a substrate on which a molecule that can be bound to a biological substance is immobilized and the biological substance is bound to the molecule, and irradiating the substrate in accordance with an irradiation pattern having a different segment with time; and a step of analyzing the biological substance on the basis of information obtained from the irradiation.

The irradiation pattern includes a pattern to irradiate one segment or a plurality of segments.

Furthermore, the irradiation pattern may include a pattern to irradiate the plurality of segments, and the irradiated segments form a shape selected from a group including linear, grid, rectangular, square, and frame shapes.

Moreover, the method may further include a step of acquiring image data of the entire substrate to determine a segmentation pattern and/or determine an irradiation pattern on the basis of distribution data of the biological substance on the substrate, the distribution data being acquired from the image data.

Furthermore, the method may further include an analyzing step of analyzing, on the basis of information obtained from the irradiation, presence/absence of the biological substance in each of the segments and/or whether or not the biological substance is a target biological substance.

Furthermore, the method may further include a biological substance releasing step of releasing the biological substance from the substrate on the basis of information obtained from the analyzing step.

Furthermore, the present technology provides a biological substance analyzer including:

a substrate on which a molecule that can be bound to a biological substance is immobilized;

an irradiation unit that irradiates the substrate; and an irradiation control unit that segments the substrate and controls the irradiation in accordance with an irradiation pattern having a different segment with time.

The biological substance analyzer can include an analysis unit that analyzes presence/absence of the biological substance in each of the segments and/or whether or not the biological substance is a target biological substance on the basis of information obtained from the irradiation in accordance with the irradiation pattern.

As the molecule that can be bound to the biological substance, a stimulus-degradable linker can be used.

Furthermore, the irradiation unit can irradiate two or more kinds of light.

Furthermore, the present technology provides a biological substance analysis program that causes a computer to execute: segmenting a substrate on which a molecule that can be bound to a biological substance is immobilized; and irradiating the substrate in accordance with an irradiation pattern having a different segment with time.

Moreover, the present technology provides a biological substance analysis system including:

a biological substance analyzer including a substrate on which a molecule that can be bound to a biological substance is immobilized, an irradiation unit that irradiates the substrate, an irradiation control unit that segments the substrate and controls the irradiation in accordance with an irradiation pattern having a different segment with time, and an analysis unit that analyzes presence/absence of the biological substance in each of the segments and/or whether or not the biological substance is a target biological substance on the basis of information obtained from the irradiation in accordance with the irradiation pattern;

a biological substance analysis program that causes a computer to execute irradiation in accordance with the irradiation pattern; and a display device that displays a result obtained from the analysis unit.

Effects of the Invention

According to the present technology, the biological substance can be densely arranged while avoiding deterioration of signal quality caused by crosstalk at the time of irradiating the substrate on which the biological substance is arranged, and as a result, it is possible to improve a throughput while securing signal reliability.

Note that the effects recited herein are not constantly limited and may be any effect recited in the present disclosure.

MODE FOR CARRYING OUT THE INVENTION

Preferred embodiments to carry out the present technology will be described below. Note that the embodiments described below illustrate representative embodiments of the present technology and the scope of the present technology should not be interpreted to be limited by these embodiments. The description will be provided in the following order.

1. Catching and Labeling Biological Substance on Substrate
   1-1. Substrate
   1-2. Labeling Biological Substance
2. Irradiating Substrate and Detecting Biological Substance
   2-1. Irradiation Mechanism
   2-2. Irradiation Pattern
   2-3. Detection Unit
3. Biological Substance Analysis Method
4. Biological Substance Analyzer
5. Biological Substance Analysis Program
6. Biological Substance Analysis System Note that, in the present technology, a biological substance includes various kinds of chemical substances existing in a living body. Examples of the chemical substances can include proteins, nucleic acids, carbohydrates, lipids, vitamins, minerals, hormones, pigments, and the like. Additionally, cells and tissues including the chemical substances are also to be included in the biological substance. The cell may be a single cell or a cell aggregation.

In the following, a description will be provided by mainly assuming that a cell including a cell surface protein is caught on a substrate, but the present technology is not limited thereto.

<1. Catching and Labeling Biological Substance on Substrate>

1-1. Substrate

A molecule that can be bound to a cell surface protein or nucleic acid that is a biological substance is immobilized on the substrate used in the present technology. Accordingly, in a case of applying a cell including a cell surface protein or the like onto the substrate, the cell can be caught on the substrate.

As the substrate, for example, a substrate including materials such as plastic, glass, and silicon can be used. In a case where the substrate on which the cell is caught is irradiated from above or below and light is made to pass through the substrate, a transparent material is preferable, and plastic and glass are preferable.

Alternatively, a solid-state imaging element (CCD, CMOS) capable of acquiring the caught cell as an image may be used as the substrate.

A molecule that can be bound to the biological substance can be selected in accordance with the biological substance. For example, in a case where the biological substance is a cell surface protein or a carbohydrate chain, it is possible to select an antibody, an alexin, an aptamer, or a molecular recognition polymer which are specific to the cell surface protein or the carbohydrate chain. In a case where the biological substance is a cell membrane lipid, it is possible to select a compound including an oleyl group that is bound to the cell membrane lipid.

Furthermore, when the biological substance is DNA or RNA, it is possible to select complementary DNA or RNA, or a nucleic acid aptamer as a molecule that can be bound to the biological substance. When the biological substance is an antigen, it is possible to select an antibody and an alexin as molecules that can be bound to the biological substance.

Examples of the antibody and the alexin can include an antibody or an alexin against a CD antigen that appears on the cell surface upon differentiation, an antibody or an alexin against various kinds of cancer-specific antigens, an antibody or an alexin against a major histocompatibility antigen, an antibody or an alexin against a carbohydrate chain.

The aptamer is a nucleic acid molecule or peptide that is specifically bound to a molecule included in a cell desired to be caught. Examples of the aptamer can include a DNA aptamer, an RNA aptamer, a peptide aptamer, a modified aptamer in which specificity is improved by introducing a modification to a nucleic acid backbone or a base, and the like.

The molecular recognition polymer catches a target cell surface molecule with high selectivity even in presence of a compound having a physicochemical property similar to that of the cell surface molecule of a cell desired to be caught. This also called a molecularly imprinted polymer and has a compound recognition region selectively synthesized.

To immobilize the molecule that can be bound to the biological substance on the substrate, it is possible to use a technology of noncovalent or covalent immobilization on a support body used for ELISA, western blotting, affinity purification, or the like. However, at the time of the immobilization, it is preferable not to increase, as much as possible, a distance from a substrate surface to the molecule that can be bound to the biological substance because the increase in the distance causes deterioration of a Signal to Noise ratio (S/N).

At the time of immobilizing the molecule that can be bound to the biological substance, it is possible to immobilize the molecule on the substrate via a stimulus-degradable linker or a polymeric substance such as collagen, PEG, or MPC, for example, while giving consideration so as not to increase the distance.

The molecule that can be bound to the biological substance may be immobilized on the substrate by initially immobilizing the stimulus-degradable linker on the substrate and then binding, to the stimulus-degradable linker, the molecule that can be bound to the biological substance. Alternatively, the polymer such as PEG or MPC may be initially immobilized on the substrate, next the stimulus-degradable linker may be bound to the polymer, and then the molecule that can be bound to the biological substance may be bound to the stimulus-degradable linker.

In a case of using the stimulus-degradable linker, the stimulus-degradable linker is cleaved by stimulating the stimulus-degradable linker located at a position on the substrate on which a desired cell is caught after catching the cell on the substrate, and the desired cell can be released and collected from the substrate.

The stimulus-degradable linker is a connecting molecule that is degraded by a specific external stimulus. For example, there is a linker that is degraded by light having a specific wavelength, a linker that is degraded by an enzyme, a linker that is degraded by a temperature, and the like. The stimulus-degradable linker is not particularly limited, but in a case of catching a single cell on the substrate, it is preferable to use a photodegradable linker from viewpoints that control can be performed per single cell and a degradation time is short.

The photodegradable linker is a molecule having a structure that is degraded by a specific wavelength.

Examples of the photodegradable linker can include: a methoxy-nitrobenzyl group; a nitrobenzyl group (Japanese Patent Application Laid-Open No. 2010-260831); a p-hydroxyphenacyl group (Tetrahedron Letters, 1962, volume 1, page 1); a 7-nitroindoline group (Journal of the American Chemical Society, 1976, volume 98, page 843); a 2-(2-nitrophenyl) ethyl group (Tetrahedron, 1997; volume 53, page 4247); a (coumarin-4-yl) methyl group (Journal of the American Chemical Society, 1984, volume 106, page 6860); and the like.

Furthermore, the photodegradable linker is specifically described as a photodegradable group, for example, in Patent Document 1 described above.

The specific wavelength at which the photodegradable linker is degraded substantially coincides with an absorption wavelength of a photodegradable molecule.

For example, in a case of a methoxy nitro-benzyl group used as the photodegradable linker, when absorption at 346 nm is assumed as 1, the absorption exhibits 0.89 at 364 nm, 0.15 at 406 nm, and 0.007 at 487 nm. In other words, when a light source of 365 nm is used, degradation efficiency of the photodegradable linker is good, and when a light source of 488 nm is used, the photodegradable linker is not substantially degraded. Thus, the wavelength of the light emitted to the photodegradable linker is to be a wavelength appropriate for each photodegradable linker. For example, the wavelength is around 330 to 450 nm.

Furthermore, the specific wavelength at which the photodegradable linker is degraded is preferably a wavelength that does not damage a biological substance. For example, in a case where the biological substance is a cell, irradiation at 30 mW/cm^2, 100 sec.→3 J/cm^2 is preferable. Particularly, a wavelength of 300 nm or less is preferably not used because the wavelength may damage the cell.

1-2. Labeling Biological Substance

A biological substance can be labeled after being caught on the substrate. For example, it is sufficient to bind, to the biological substance on the substrate, an antibody, an alexin, an aptamer, a molecular recognition polymer, an oleyl group, or the like which is specific to the biological substance and labeled.

Alternatively, a biological substance that has been labeled in advance may be caught on the substrate. In a case of labeling the biological substance in advance, it is sufficient to make the biological substance such as a labeled protein or labeled nucleic acid contact a cell and perform operation to introduce the biological substance into the cell.

As the label, a fluorescent compound, an enzyme, biotin, a metal, or the like can be used. The fluorescent compound can be detected by using emitted light having a specific wavelength. The enzyme can be detected by coloring the enzyme with an enzyme substrate. The biotin can be detected by coloring an avidin complex bound to a fluorescent dye or the like. The metal can be detected by irradiation at a specific wavelength.

Furthermore, a bioluminescent compound, a chemiluminescent compound, a radioactive isotope, or the like may also be used as the label. In a case of these labels, it is sufficient to detect emitted light having the specific wavelength.

<2. Irradiating Substrate and Detecting Biological Substance>

When a biological substance caught on a substrate is irradiated, the substrate is segmented and irradiation is performed in accordance with an irradiation pattern having a different segment with time. In other words, a different segment is irradiated at different timing, but the timing and the segment are patterned in various manners.

Exemplary shapes of segmentation can include a grid-like shape or a honeycomb-like shape, but not limited thereto. Furthermore, a size, the number, and the like of the segmentation can be optimally selected. For the optimal selection thereof, image data of an entire substrate is acquired by a later-described biological substance method described later, and the optimal section can be determined on the basis of distribution data of the biological substance on the substrate.

Furthermore, specific examples of the irradiation pattern will be described later.

Note that the irradiation may be performed from above the substrate or may be performed from below the substrate.

2-1. Irradiation Mechanism

For example, in a case of using a fluorescent compound as a label, excitation light appropriate for the fluorescent compound is emitted, and as an irradiation mechanism at the time of such irradiation, it is possible to use an irradiation device using, for example, a transmissive liquid crystal device, a reflective liquid crystal device, a digital micromirror device (DMD), a shutter of micro electro mechanical systems (MEMS), or the like.

As the liquid crystal device, it is possible to use, for example, a silicon X-tal reflective display that drives millions or more pixels on a silicon substrate. A liquid crystal device of type 0.74 (diagonal 18.8 mm) is already developed.

As the DMD, a known DMD can be used. Assuming that the DMD can perform, for example, control (ON/OFF of the irradiation) for 1920×1080 sites at the same time, approximately $2 \times 10^6$ cells can be individually controlled at the same time.

The MEMS shutter does not include a color filter or a polarizing film that transmits light from a backlight like a liquid crystal device, and includes a shutter that directly transmits light (red light, green light, and blue light) of the backlight.

As the MEMS shutter, a known MEMS shutter can be used. For example, it is possible to exemplify a MEMS shutter having a laminated structure (sequentially laminating, from a lower side, a light source, a light guide plate, a polarizing plate, an array substrate, a transparent electrode (sub-pixel electrode), an alignment film, a liquid crystal layer, an alignment film, a transparent electrode (common electrode), a color filter substrate, and a polarizing plate).

According to the irradiation mechanism, irradiation can be controlled per segment. The irradiation mechanism is not particularly limited as far as the irradiation mechanism can control a region and a time of a two-dimensional irradiation pattern described later.

Furthermore, the irradiation mechanism may determine whether or not to irradiation each segment after confirming a segment in which a biological substance is caught, and may control the irradiation. For example, in a case of using an image pick-up device in the substrate and catching a biological substance on the substrate as described above, the caught biological substance in each segment can be found from an image, and it is possible to obtain data to be a basis of determining whether or not to irradiate each segment.

2-2. Irradiation Pattern

The substrate is irradiated in accordance with an irradiation pattern in which whether or not to irradiate each segment is patterned so as to reduce a crosstalk problem.

Figure 4:
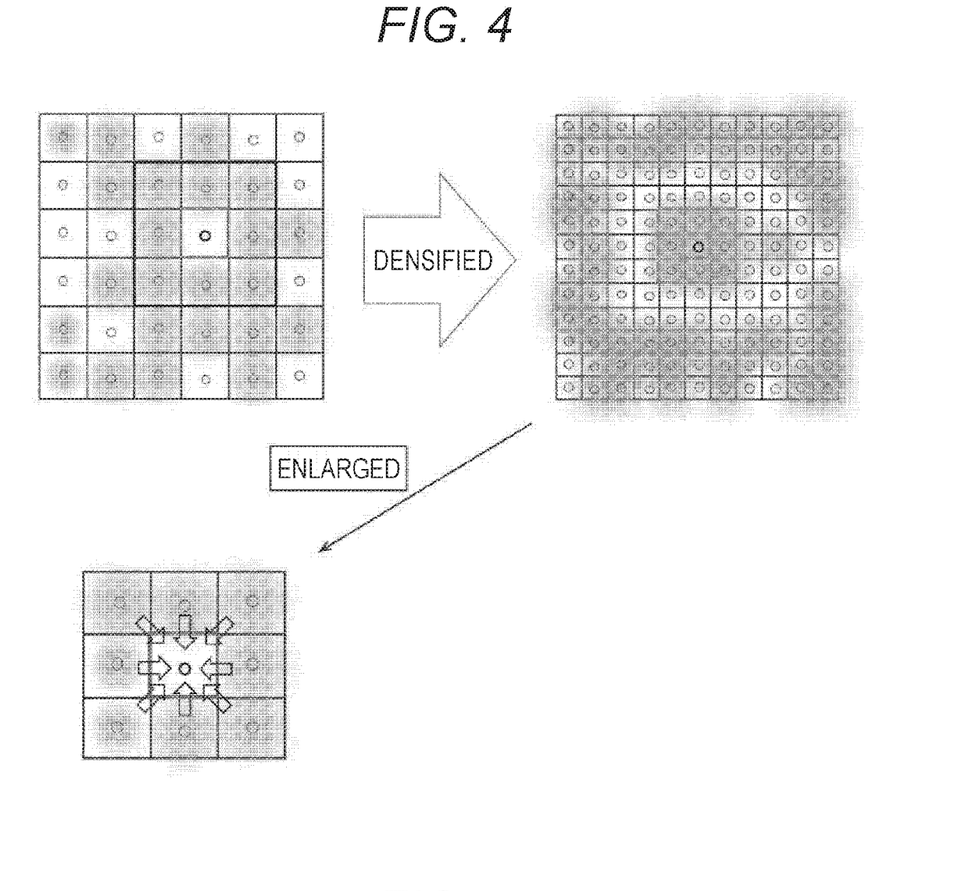
FIG. 4 is a view illustrating an irradiation pattern affected by the crosstalk.

Here, an irradiation pattern that is considered to be strongly affected by the crosstalk is illustrated in FIG. 4.

An upper left diagram in FIG. 4 is the irradiation pattern not considering the crosstalk. To perform processing at a high throughput, molecules that can be bound to the biological substance are densely immobilized on the substrate and then the biological substance is caught as illustrated in an upper right diagram in FIG. 4. However, when the substrate is densified, influence of the crosstalk of fluorescent-labeled signals from segments that contact a periphery of a central segment becomes strong (a lower left diagram in FIG. 4).

Particularly, there is strong influence of the crosstalk from the segments that lengthwise and crosswise contact the central segment (the lower left diagram in FIG. 4). It is considered that there is relatively little influence from the fluorescent-labeled signals from the segments that obliquely contact the central segment.

Figure 5:
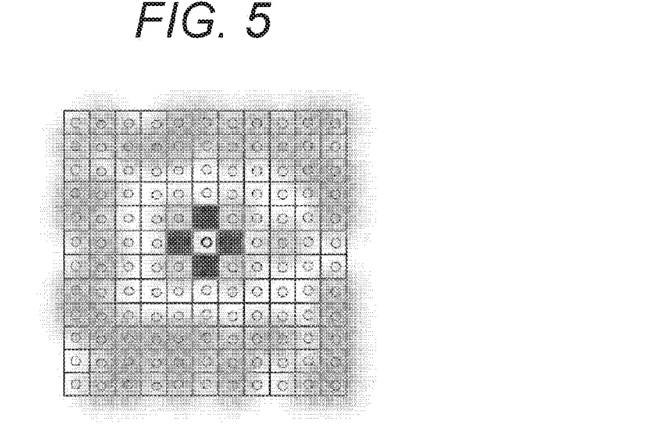
FIG. 5 is a diagram illustrating an irradiation pattern of the present technology.

Accordingly, to detect a fluorescent-labeled signal of the central segment while reducing the influence of the crosstalk, it is advisable, as illustrated in FIG. 5, to adopt an irradiation pattern (a shutter is closed in each of black-colored segments in the drawing) to control the irradiation mechanism such that the central segment is irradiated but the segments that lengthwise and crosswise contact the central segment are not irradiated on the densified substrate.

Figure 6:
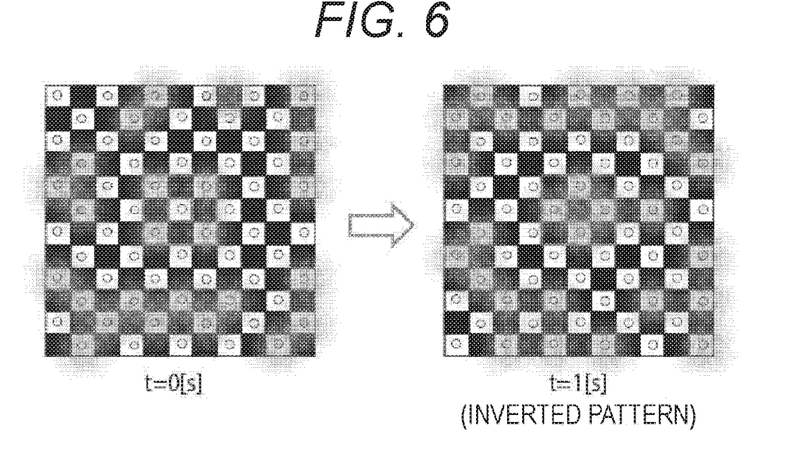
FIG. 6 is a diagram illustrating an irradiation pattern of the present technology.

When the irradiation pattern is patterned so as to be able to irradiate the entire surface at a time, a grid pattern illustrated in FIG. 6 is obtained, for example.

First, the substrate is irradiated in accordance with a left grid pattern in FIG. 6 (time t=0[S]). Next, the substrate is irradiated in accordance with a pattern (time t=1[S]) obtained by inverting the left grid pattern in FIG. 6. Thus, when the irradiation is performed at different timing in accordance with the inverted pattern, the influence of the crosstalk can be reduced at the time of detecting the fluorescent-labeled signals before and after the inversion, and it is possible to correctly identify a segment in which a target biological substance is caught.

Figure 7:
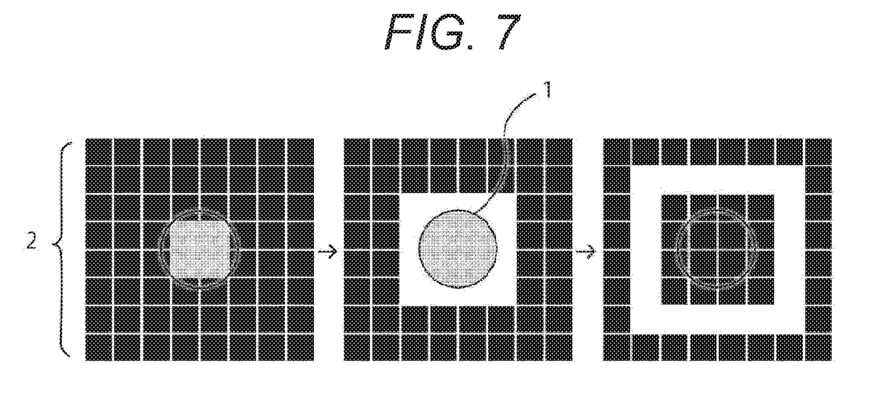
FIG. 7 is a diagram illustrating an irradiation pattern of the present technology.
Figure 8:
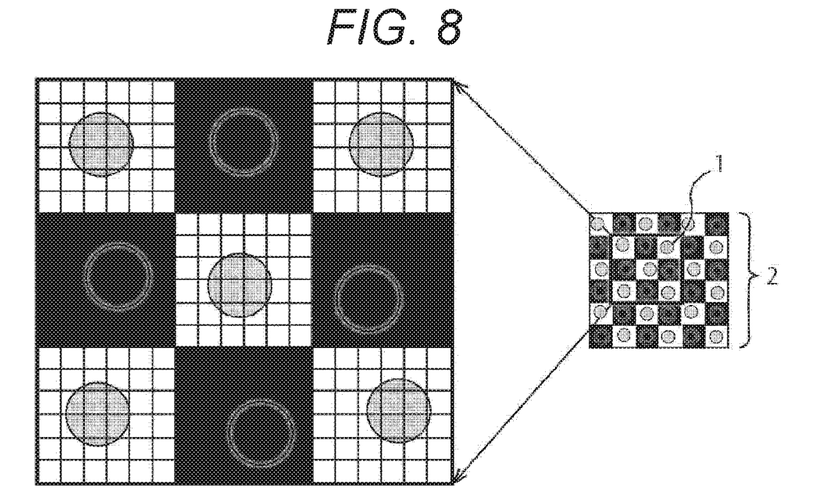
FIG. 8 is a diagram illustrating an irradiation pattern of the present technology.
Figure 9:
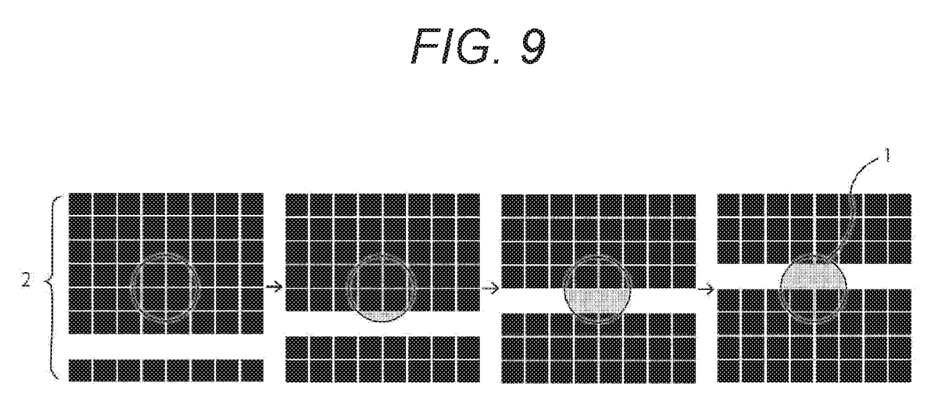
FIG. 9 is a diagram illustrating an irradiation pattern of the present technology.

Besides the above-described grid pattern, irradiation patterns illustrated in FIGS. 7 to 9 may also be exemplified, but the present technology is not limited to these irradiation patterns. Examples of the irradiation pattern can include a pattern that forms a shape selected from a group including linear, grid, rectangular, square, and frame shapes.

FIG. 7 illustrates irradiation patterns in a case where a cell including a cell surface protein that is the biological substance is larger than one segment of the substrate.

A left diagram in FIG. 7 illustrates an irradiation pattern (square (small) pattern) in which a fluorescent-labeled cell 1 larger than one segment of a substrate 2 is caught and segments overlapping with the fluorescent-labeled cell 1 are partly irradiated.

A central diagram in FIG. 7 is an irradiation pattern (square (large) pattern) in which the irradiation is performed for a region including the segments overlapping with the fluorescent-labeled cell 1.

A right diagram in FIG. 7 is an irradiation pattern (frame pattern) in which the irradiation is performed for a region not including the segments overlapping with the fluorescent-labeled cell 1.

Since the irradiation is performed at different timing in accordance with the respective left, central, and right irradiation patterns of FIG. 7, it is possible to obtain a more accurate signal while reducing the crosstalk problem. The order of these irradiation patterns is not particularly limited.

Furthermore, in the frame pattern, when the irradiation is performed from the cell side, illumination becomes oblique in combination with a diffusion plate of the irradiation mechanism, and absorption of the excitation light is increased. Therefore, improvement of the Signal to Noise ratio (S/N) is expected.

FIG. 8 illustrates an irradiation pattern of a substrate on which a large number of molecules that can be bound to a cell substance are immobilized.

A right diagram in FIG. 8 illustrates the irradiation pattern (grid pattern) of the entire substrate.

A left diagram of FIG. 8 illustrates an enlarged view of the irradiation pattern.

Besides the grid pattern illustrated in FIG. 8, irradiation can be performed in accordance with various kinds of patterns such as a linear pattern described below.

FIG. 9 illustrates an example of the linear pattern.

As illustrated from left to right in FIG. 9, linear irradiation can be performed from a segment not overlapping with the fluorescent-labeled cell 1 to a segment overlapping with the fluorescent-labeled cell at different timing.

2-3. Detection Unit

A biological substance captured on a substrate can be detected by a detection unit that receives a signal from a label of the biological substance.

Examples of the detection unit can include a fluorometry device, a scattered light measurement device, a transmitted light measurement device, a reflected light measurement device, a diffracted light measurement device, an ultraviolet spectrometer, an infrared spectrometer, a Raman spectrometer, a FRET measurement device, a FISH measurement device, other various spectrum measurement devices, a so-called multi-channel light detector in which a plurality of light detectors is arranged in an array, and the like. Furthermore, a solid-state imaging device (CCD, CMOS) or the like that can detect the biological substance as image data may also be used. The detection unit of the present technology is not limited thereto.

<3. Biological Substance Analysis Method>

A biological substance analysis method using the irradiation method of the present technology includes:

a step of segmenting a substrate on which a molecule that can be bound to a biological substance is immobilized and the biological substance is bound to the molecule, and irradiating the substrate in accordance with an irradiation pattern having a different segment with time; and a step of analyzing the biological substance on the basis of information obtained from the irradiation.

As one embodiment, the method can include:

segmenting the substrate after making a sample that may include the biological substance contact the substrate and be bound to the substrate; for example, a step of performing irradiation in accordance with a first irradiation pattern;

a step of performing irradiation in accordance with a second irradiation pattern; and a step of analyzing the biological substance on the basis of information obtained from the irradiation in accordance with the first irradiation pattern and the second irradiation pattern.

Figure 10:
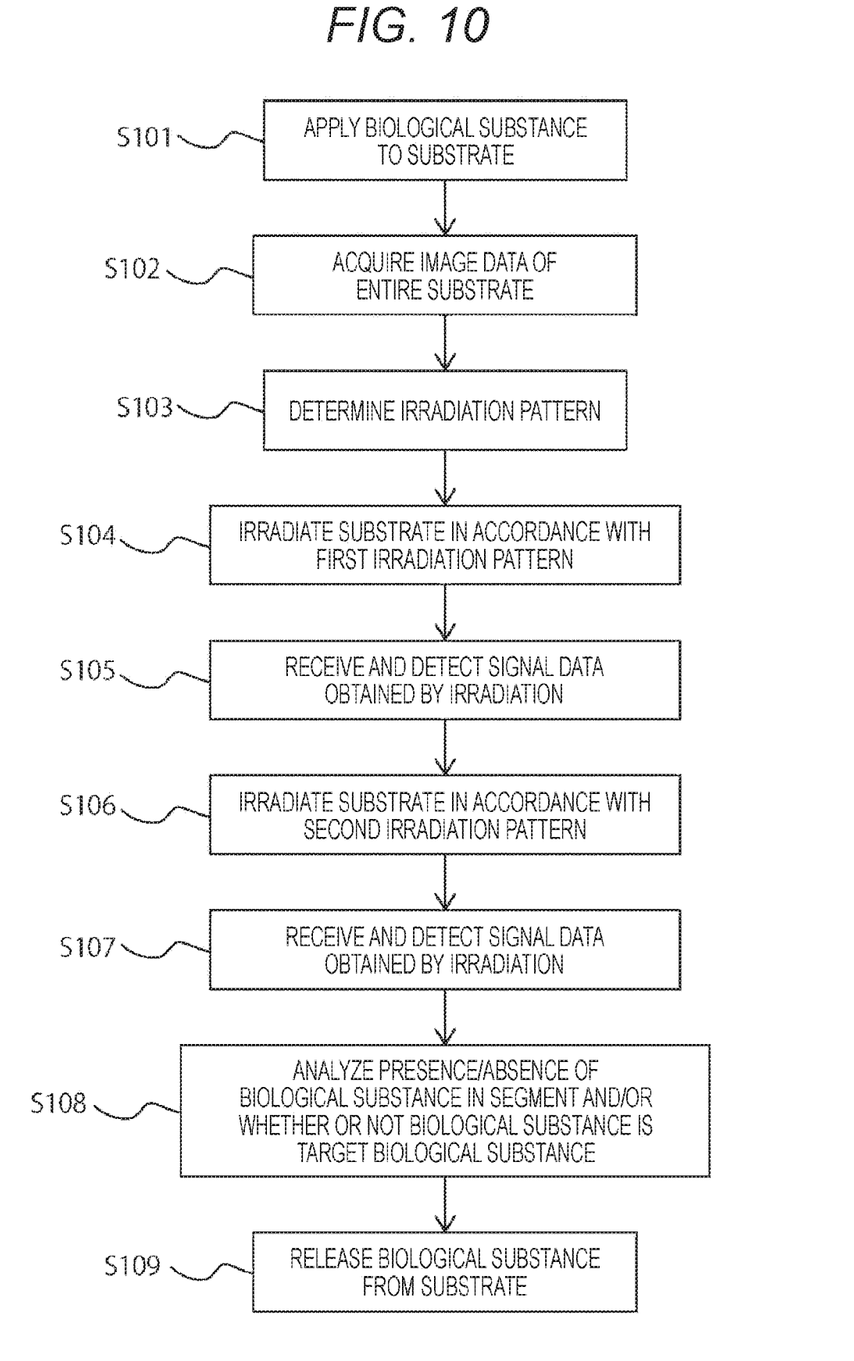
FIG. 10 is a diagram illustrating a biological substance analysis method of the present technology.

The biological substance analysis method of the present technology can be performed by steps illustrated in FIG. 10, for example.

First, a sample including a biological substance is applied to a substrate (S101), and a molecule that can be bound to the biological substance on the substrate is made to contact the sample. After the biological substance inside the sample is caught on the substrate, an unnecessary sample is removed by cleaning or the like.

Next, image data of the entire substrate is acquired (S102), and it is possible to include a step of recognizing in which one of segments the biological substance is caught. The image data may be acquired by one-dimensional scanning or acquired as a two-dimensional plane, but acquisition as the plane can be selected from a viewpoint of time-saving.

Alternatively, after acquiring the image data of the entire substrate (S102), it may be possible to include a step of determining a segmentation pattern from a finding of distribution of the biological substance on the substrate. This is a step of determining a shape, a size, the number, and the like of the segmentation.

Furthermore, an irradiation pattern can also be selected from image data (S103).

An optimal segmentation pattern and an optimal irradiation pattern can be selected from segmentation patterns and irradiation patterns stored in advance in a storage medium, or an optimal segmentation pattern and an optimal irradiation pattern can also be selected by calculation from a distribution density by using a calculation program. A known image processing program may also be used. Furthermore, the substrate may be divided in accordance with a level of the distribution density, a region having a high distribution density may be finely segmented and a region having a low distribution density may be roughly segmented. Moreover, the optimal segmentation pattern and the optimal irradiation pattern can be selected by performing image data processing several times and making a computer learn the patterns.

Note that the irradiation pattern can be determined from one pattern or by appropriately combining two or more patterns. The substrate is irradiated in accordance with the determined irradiation pattern (S104). Signal data generated by the irradiation and obtained from a label of the biological substance is received and detected by the detection unit (S105).

Note that when the two or more patterns are adopted, the substrate is irradiated in accordance with the respective patterns while providing a time difference. Referring to FIG. 10, the substrate is irradiated in accordance with a second irradiation pattern (S106), and signal data generated by the irradiation and obtained from the label of the biological substance is received and detected by the detection unit (S107).

The biological substance analysis method of the present technology may include an analyzing step of analyzing presence/absence of the biological substance in each segment on the basis of the information obtained by the detection unit (S108). Furthermore, in a case where there is the biological substance in each segment, it may be possible to include an analyzing step of analyzing whether or not the biological substance is a target biological substance desired to be acquired (S108).

Moreover, the biological substance analysis method of the present technology may include a biological substance releasing step of releasing the biological substance from the substrate on the basis of the information obtained from the analysis step (S109). To release the biological substance from the substrate, for example, it is sufficient to stimulate a stimulus-degradable linker interposed between the substrate and the molecule that can be bound to the biological substance. A specific example thereof can include irradiating, with light having a wavelength specific to the photodegradable linker, only a segment including the biological substance desired to be released. Here, the biological substance desired to be released can be a target biological substance or a non-target biological substance.

The irradiation pattern can also be used in the biological substance releasing step (S109). When irradiation is performed in accordance with the irradiation pattern, releasing accuracy of the biological substance can be improved, similar to the reduction effect of the crosstalk at the time of the fluorescence measurement.

For example, there is a case where a target biological substance desired to remain without being released is surrounded by a non-target biological substance desired to be released.

In such a case, a light emitting amount to the target biological substance can be reduced by irradiating the substrate with light having a wavelength specific to the photodegradable linker in accordance with an irradiation pattern similar to an irradiation pattern at the time of the fluorescence measurement, and accuracy of releasing and sorting of the target biological substance or the non-target biological substance is improved.

In a case where the released biological substance is the target biological substance, the biological substance is collected and used for further steps, for example, analysis, proliferation, magnification, and the like. In a case where the released biological substance is the non-target biological substance, the released biological substance is discarded as it is, and the target biological substance remaining on the substrate is used for the further steps on the substrate.

<4. Biological Substance Analyzer>

An apparatus that implements the biological substance analysis method of the present technology includes:

a substrate on which a molecule that can be bound to a biological substance is immobilized;

an irradiation unit that irradiates the substrate; and an irradiation control unit that segments the substrate and controls the irradiation in accordance with an irradiation pattern having a different segment with time.

Figure 11:
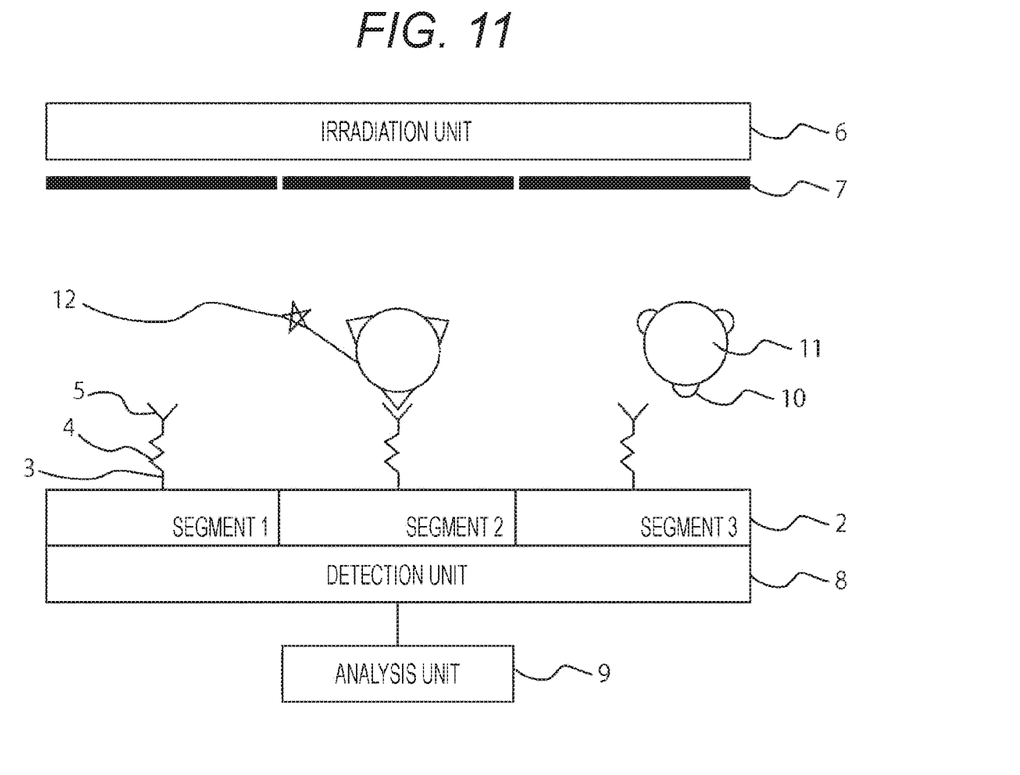
FIG. 11 is a diagram illustrating a biological substance analyzer of the present technology.

FIG. 11 illustrates an exemplary biological substance analyzer.

A substrate 2 includes a plurality of segments, and a polymeric substance 3 (collagen, PEG, MPC, or the like), a stimulus-degradable linker 4 (photodegradable linker or the like), a molecule 5 (antibody, complementary DNA, aptamer, or the like) that can be bound to a biological substance are immobilized in each of the segments. A cell 11 is applied to the substrate 2, a biological substance 10 (cell surface protein, nucleic acid, or the like) on the cell 11 is bound to the molecule 5 that can be bound to the biological substance, and the cell 11 is caught. The caught cell 11 is labeled with a label 12 (fluorescent substance or the like).

Here, whether or not the cell 11 is captured in each of the segments may be detected by image data or the like. Detection can be performed by a detection unit 8. For example, the detection unit 8 includes a solid-state imaging device, and an irradiation pattern is determined on the basis of the image data.

The irradiation pattern can be implemented by an irradiation unit 6 and an irradiation control unit 7. The irradiation unit 6 emits light having a wavelength appropriate for the label 12. The irradiation unit 6 may be able to emit a plurality of kinds of light having different wavelengths. Examples of the irradiation light can include: light having a wavelength suitable for observing whether or not the biological substance is bound to each of the segments; light having a wavelength that excites the label 12; light that cleaves the photodegradable linker; and the like.

The irradiation control unit 7 (a transmissive liquid crystal device, a reflective liquid crystal device, a DMD, a MEMS shutter, or the like) controls the light from the irradiation unit 6 in accordance with the determined irradiation pattern. The irradiation pattern is executed by a shutter mechanism, a digital mirror device, or the like included in the irradiation control unit 7.

The detection unit 8 receives and detects signal data and the like obtained by the irradiation in accordance with the irradiation pattern. An analysis unit 9 analyzes presence/absence of the biological substance or the cell in each of the segments and/or whether or not the biological substance or the cell is a target biological substance or a target cell on the basis of information of the obtained signal data.

<5. Biological Substance Analysis Program>

A biological substance analysis program of the present technology causes a computer to execute: segmenting a substrate on which a molecule that can be bound to a biological substance is immobilized; and irradiating the substrate in accordance with an irradiation pattern having a different segment with time. Specifically, the program is programmed so as to execute the above-described irradiation pattern.

The biological substance analysis program may be stored in a recording medium such as a magnetic disk, an optical disc, a magneto-optical disc, or a flash memory, for example, and also the biological substance analysis program may be distributed via a network. The biological substance analysis program may execute analysis by externally attaching the computer to the biological substance analyzer, or may be executed by being incorporated in the biological substance analyzer.

<6. Biological Substance Analysis System>

A biological substance analysis system of the present technology includes:

a biological substance analyzer including: a substrate on which a molecule that can be bound to a biological substance is immobilized; an irradiation unit that irradiates the substrate; an irradiation control unit that segments the substrate and controls the irradiation in accordance with an irradiation pattern having a different segment with time; and an analysis unit that analyzes presence/absence of the biological substance in each of the segments and/or whether or not the biological substance is a target biological substance on the basis of information from the irradiation in accordance with the irradiation pattern;

a biological substance analysis program that causes a computer to execute irradiation in accordance with the irradiation pattern; and a display device that displays a result obtained from the analysis unit.

Figure 12:
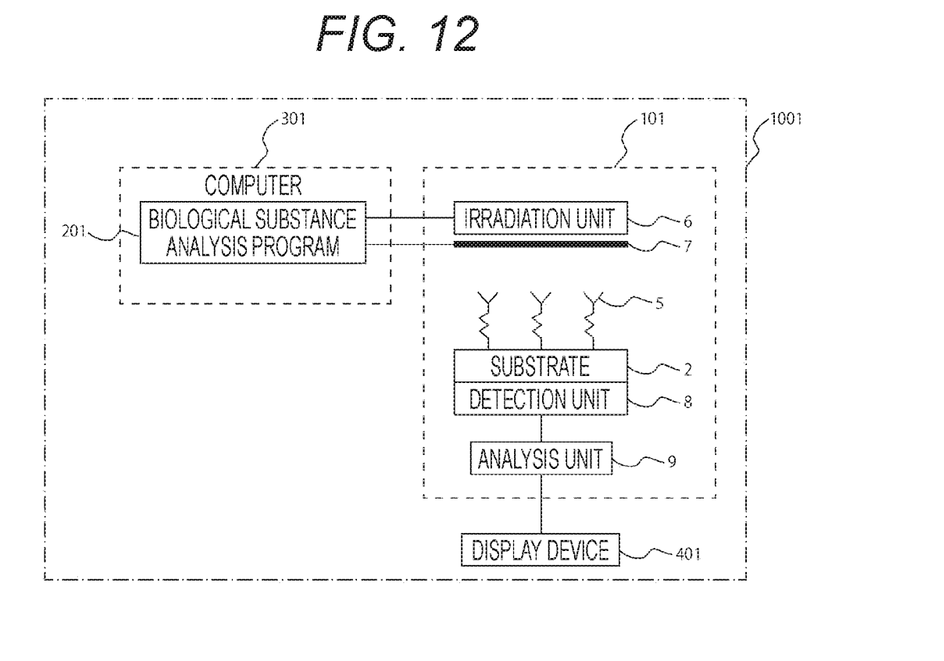
FIG. 12 is a diagram illustrating a biological substance analysis system of the present technology.

FIG. 12 illustrates an exemplary biological substance analysis system.

A biological substance analysis system 1001 includes a biological substance analyzer 101, a computer 301, and a display device 401.

The biological substance analyzer 101 includes the irradiation unit 6, the irradiation control unit 7, the molecule 5 that can be bound to the biological substance, the substrate 2, the detection unit 8, and the analysis unit 9.

The computer 301 includes a biological substance analysis program 201. The biological substance analysis program 201 communicates with the irradiation unit 6 and the irradiation control unit 7.

The display device 401 is connected to the analysis unit 9 of the biological substance analyzer 101. Examples of the display unit 401 can include a monitor and a printing device. By performing mouse operation, keyboard operation, and the like in the computer 301, the sample is applied to the substrate 2, and it is possible to arbitrarily or automatically control the irradiation unit 6, the irradiation control unit 7, the detection unit 8, the analysis unit 9, the biological substance analysis program 201, and the like on the basis of analysis data and the like displayed on the monitor or a print.

Note that the present technology can also adopt the following configurations.

[1] A biological substance analysis method including:

a step of segmenting a substrate on which a molecule that can be bound to a biological substance is immobilized and the biological substance is bound to the molecule, and irradiating the substrate in accordance with an irradiation pattern having a different segment with time; and a step of analyzing the biological substance on the basis of information obtained from the irradiation.

[2] The biological substance analysis method recited in [1], in which the irradiation pattern includes a pattern to irradiate one segment or a plurality of segments.

[3] The biological substance analysis method recited in [2], in which the irradiation pattern includes a pattern to irradiate the plurality of segments, and the irradiated segments form a shape selected from a group including linear, grid, rectangular, square, and frame shapes.

[4] The biological substance analysis method recited in any one of [1] to [3], further including a step of acquiring image data of the entire substrate to determine a segmentation pattern and/or determine an irradiation pattern on the basis of distribution data of the biological substance on the substrate, the distribution data being acquired from the image data.

[5] The biological substance analysis method recited in any one of [1] to [4], further including an analyzing step of analyzing, on the basis of information obtained from the irradiation, presence/absence of the biological substance in each of the segments and/or whether or not the biological substance is a target biological substance.

[6] The biological substance analysis method recited in [5], further including a biological substance releasing step of releasing the biological substance from the substrate on the basis of information obtained from the analyzing step.

[7] A biological substance analyzer including:

a substrate on which a molecule that can be bound to a biological substance is immobilized;

an irradiation unit that irradiates the substrate; and an irradiation control unit that segments the substrate and controls the irradiation in accordance with an irradiation pattern having a different segment with time.

[8] The biological substance analyzer recited in [7], further including an analysis unit that analyzes presence/absence of the biological substance in each of the segments and/or whether or not the biological substance is a target biological substance on the basis of information obtained from the irradiation in accordance with the irradiation pattern.

[9] The biological substance analyzer recited in [7] or [8], in which the molecule that can be bound to the biological substance is a stimulus-degradable linker.

[10] The biological substance analyzer recited in any one of [7] to [9], in which the irradiation unit can irradiate two or more kinds of light.

[11] A biological substance analysis program causing a computer to execute: segmenting a substrate on which a molecule that can be bound to a biological substance is immobilized; and irradiating the substrate in accordance with an irradiation pattern having a different segment with time.

[12] A biological substance analysis system including:
a biological substance analyzer including
a substrate on which a molecule that can be bound to a biological substance is immobilized,
an irradiation unit that irradiates the substrate,
an irradiation control unit that segments the substrate and controls the irradiation in accordance with an irradiation pattern having a different segment with time, and
an analysis unit that analyzes presence/absence of the biological substance in each of the segments and/or whether or not the biological substance is a target biological substance in accordance with information obtained from the irradiation on the basis of information obtained from the irradiation in accordance with the irradiation pattern;
a biological substance analysis program that causes a computer to execute irradiation in accordance with the irradiation pattern; and
a display device that displays a result obtained from the analysis unit.

REFERENCE SIGNS LIST

1 Fluorescent-labeled cell
2 Substrate
3 Polymeric substance
4 Stimulus-degradable linker
5 Molecule that can be bound to biological substance
6 Irradiation unit
7 Irradiation control unit
8 Detection unit
9 Analysis unit
10 Biological substance
11 Cell
12 Label
101 Biological substance analyzer
201 Biological substance analysis program
301 Computer
401 Display device
1001 Biological substance analysis system

The invention claimed is:

1. A biological substance analysis method, comprising:
segmenting a substrate that includes a molecule bondable to a biological substance, wherein the molecule is immobilized on the substrate;
acquiring image data of an entire surface of the substrate;
acquiring distribution data of the biological substance on the substrate based on the acquired image data;
determining a segmentation pattern of the substrate based on the acquired distribution data;
determining a first irradiation pattern and a second irradiation pattern based on the acquired distribution data;
irradiating the substrate with the first irradiation pattern at a first time instant;
irradiating the substrate with the second irradiation pattern at a second time instant, wherein the second irradiation pattern is inverted with respect the first irradiation pattern; and
analyzing the biological substance based on information obtained from the irradiation of the substrate with the first irradiation pattern and the second irradiation pattern.

2. The biological substance analysis method according to claim 1, wherein each of the first irradiation pattern and the second irradiation pattern includes a pattern to irradiate at least one segment of a plurality of segments of the substrate.

3. The biological substance analysis method according to claim 2, wherein
each of the first irradiation pattern and the second irradiation pattern includes the pattern to irradiate the plurality of segments of the substrate, and
the plurality of segments form a shape that includes at least one of a linear shape, a grid shape, a rectangular shape, a square shape, or a frame shape.

4. The biological substance analysis method according to claim 1, further comprising:
analyzing, based on the information obtained from the irradiation of the substrate with the first irradiation pattern and the second irradiation pattern, one of presence or absence of the biological substance in each segment of a plurality of segments of the substrate; and
analyzing whether or not the biological substance is a target biological substance based on the information obtained from the irradiation of the substrate with the first irradiation pattern and the second irradiation pattern.

5. The biological substance analysis method according to claim 4, further comprising releasing the biological substance from the substrate based on information obtained from the analysis of the biological substance.

6. A biological substance analyzer, comprising:
a substrate that includes a molecule bondable to a biological substance, wherein the molecule is immobilized on the substrate;
a light source configured to irradiate the substrate; and
a computer configured to:
segment the substrate;
acquire image data of an entire surface of the substrate;
acquire distribution data of the biological substance on the substrate based on the acquired image data;
determine a segmentation pattern of the substrate based on the acquired distribution data;
determine a first irradiation pattern and a second irradiation pattern based on the acquired distribution data;
control the irradiation of the substrate with the first irradiation pattern at a first time instant;
control the irradiation of the substrate with the second irradiation pattern at a second time instant, wherein the second irradiation pattern is inverted with respect to the first irradiation pattern; and
analyze the biological substance based on information obtained from the irradiation of the substrate with the first irradiation pattern and the second irradiation pattern.

7. The biological substance analyzer according to claim 6, wherein the computer is further configured to:
analyze one of presence or absence of the biological substance in each segment of a plurality of segments of the substrate, wherein the analysis is based on the information obtained from the irradiation of the substrate with the first irradiation pattern and the second irradiation pattern; and
analyze whether or not the biological substance is a target biological substance based on the information obtained from the irradiation of the substrate with the first irradiation pattern and the second irradiation pattern.

8. The biological substance analyzer according to claim 6, wherein the molecule is a stimulus-degradable linker.

9. The biological substance analyzer according to claim 6, wherein the light source is configured to irradiate a plurality of types of light.

10. A non-transitory computer-readable medium having stored thereon computer-executable instructions which, when executed by a processor, cause the processor to execute operations, the operations comprising:

segmenting a substrate that includes a molecule bondable to a biological substance, wherein the molecule is immobilized on the substrate;

acquiring image data of an entire surface of the substrate;

acquiring distribution data of the biological substance on the substrate based on the acquired image data;

determining a segmentation pattern of the substrate based on the acquired distribution data;

determining a first irradiation pattern and a second irradiation pattern based on the acquired distribution data;

irradiating the substrate with the first irradiation pattern at a first time instant;

irradiating the substrate with the second irradiation pattern at a second time instant, wherein the second irradiation pattern is inverted with respect the first irradiation pattern; and     analyzing the biological substance based on information obtained from the irradiation of the substrate with the first irradiation pattern and the second irradiation pattern.

11. A biological substance analysis system, comprising:

a biological substance analyzer that includes a substrate, wherein         the substrate includes a molecule bondable to a biological substance, and         the molecule is immobilized on the substrate;

a light source configured to irradiate the substrate;

a computer configured to:

segment the substrate;

acquire image data of an entire surface of the substrate;

acquire distribution data of the biological substance on the substrate based on the acquired image data;

determine a segmentation pattern of the substrate based on the acquired distribution data;

determine a first irradiation pattern and a second irradiation pattern based on the acquired distribution data;

control the irradiation of the substrate with the first irradiation pattern at a first time instant;

control the irradiation of the substrate with the second irradiation pattern at a second time instant, wherein the second irradiation pattern is inverted with respect to the first irradiation pattern; and         analyze, based on information obtained from the irradiation of the substrate with the first irradiation pattern and the second irradiation pattern, one of presence or absence of the biological substance in each segment of a plurality of segments of the substrate; and         analyze whether or not the biological substance is a target biological substance based on the information obtained from the irradiation of the substrate with the first irradiation pattern and the second irradiation pattern; and     a display device configured to display a result based on the analysis of the biological substance.

\* \* \* \* \*